US011813134B1

United States Patent
VanBrunt

(10) Patent No.: US 11,813,134 B1
(45) Date of Patent: Nov. 14, 2023

(54) DENTAL CROWN HOLDER

(71) Applicant: Corbyn L. VanBrunt, D.D.S., P.C., dba Smiles of Tulsa, Tulsa, OK (US)

(72) Inventor: Corbyn L. VanBrunt, Tulsa, OK (US)

(73) Assignee: Corbyn L. VanBrunt, D.D.S., P.C., Tulsa, OK (US)

( * ) Notice: Subject to any disclaimer, the term of this patent is extended or adjusted under 35 U.S.C. 154(b) by 632 days.

(21) Appl. No.: 16/777,163

(22) Filed: Jan. 30, 2020

Related U.S. Application Data

(60) Provisional application No. 62/798,564, filed on Jan. 30, 2019.

(51) Int. Cl.
*A61C 5/77* (2017.01)
*A61K 6/30* (2020.01)
*A61C 13/15* (2006.01)

(52) U.S. Cl.
CPC ............... *A61C 5/77* (2017.02); *A61C 19/004* (2013.01); *A61K 6/30* (2020.01)

(58) Field of Classification Search
CPC ........... A61C 5/77; A61C 19/004; A61K 6/30; A61C 8/0089; A61C 13/12
See application file for complete search history.

(56) References Cited

U.S. PATENT DOCUMENTS 5,735,692 A * 4/1998 Berger .................. A61C 13/20
433/213

FOREIGN PATENT DOCUMENTS

| CN | 107427414 A | * | 12/2017 | .................. A61K 6/00 |
| DE | 19847259 A1 | * | 4/2000 | ............... A61C 13/277 |

* cited by examiner

*Primary Examiner* — Nicholas D Lucchesi
(74) *Attorney, Agent, or Firm* — Head, Johnson, Kachigian & Wilkinson, PC

(57) ABSTRACT

A holder for a dental crown. The dental crown holder may comprise a handle and a working end, where the working end has at least one extension arm extending therefrom. The dental crown holder may be used by covering the working end of the dental crown holder, including the extension arms, in a curable material; placing the dental crown into the curable material such that at least a portion of the extension arms and at least a portion of the curable material are located inside an interior surface of the dental crown; and curing the curable material. The dental crown holder with cured curable material may thus securely hold the dental crown without any slipping, rotating, or wobbling, allowing the user to make adjustments to the dental crown while holding the handle of the dental crown holder rather than the dental crown itself.

5 Claims, 4 Drawing Sheets

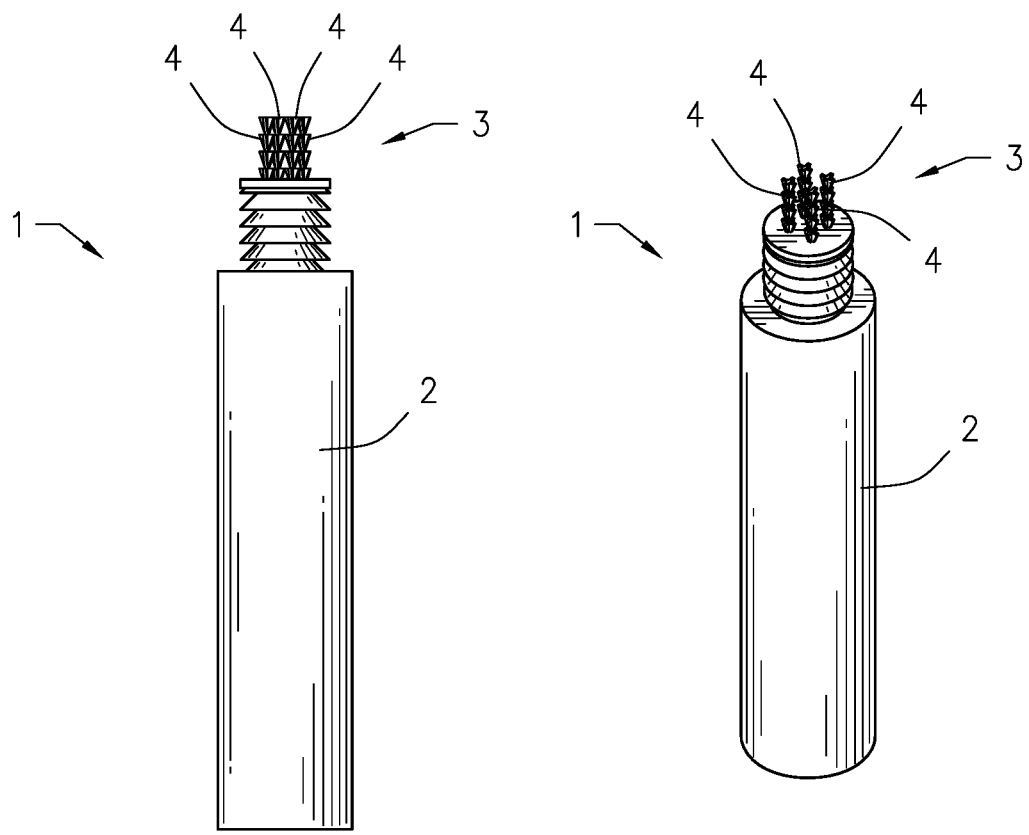
FIG. 1
FIG. 2
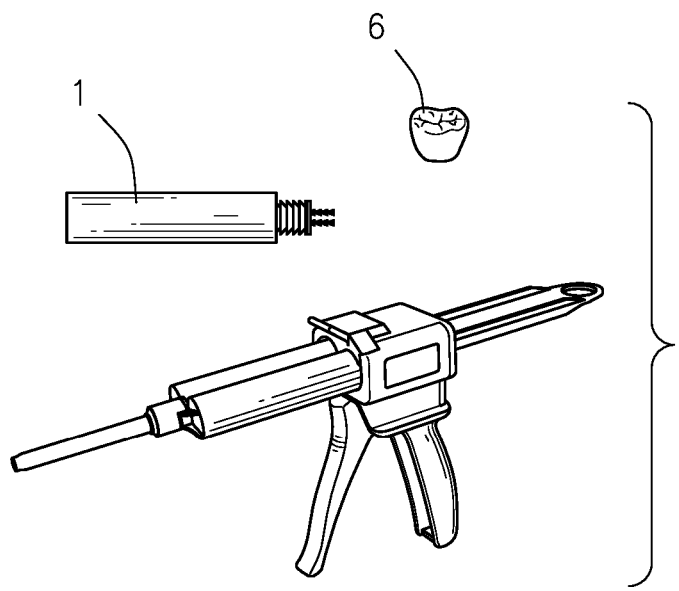
FIG. 3

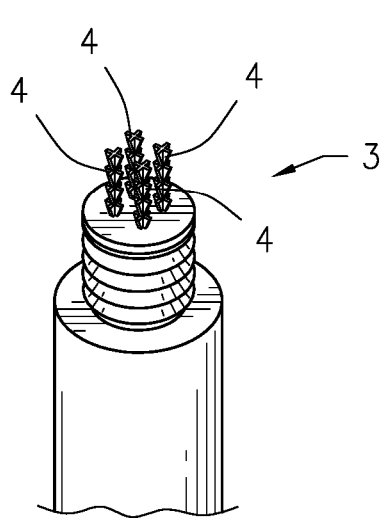
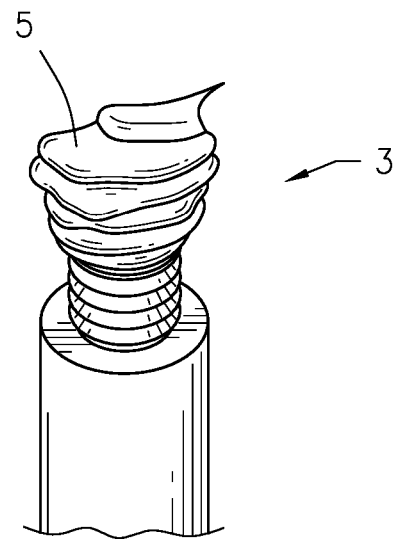
FIG. 4
FIG. 5
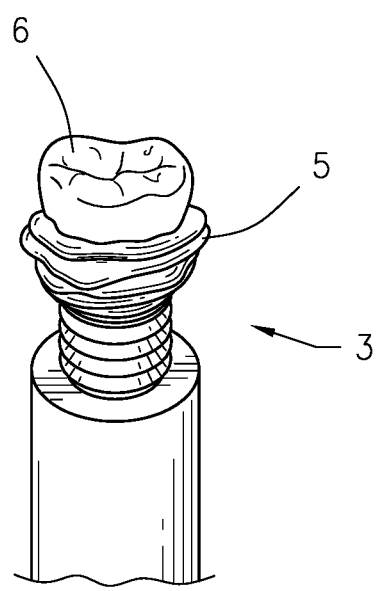
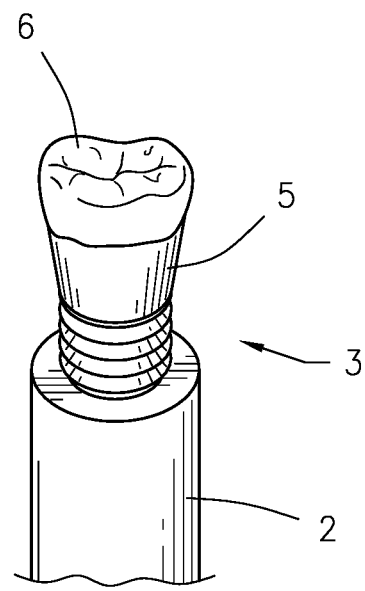
FIG. 6
FIG. 7

DENTAL CROWN HOLDER

BACKGROUND OF THE INVENTION

CROSS REFERENCE

This application is based on and claims priority to U.S. Provisional Pat. Application No. 62/798,564 filed Jan. 30, 2019.

FIELD OF THE INVENTION

This invention relates generally to dental equipment and more particularly, but not by way of limitation, to a temporary holder for a dental crown.

DESCRIPTION OF THE RELATED ART

A dental crown is a tooth-shaped cover placed over an existing, typically damaged tooth. A dental crown may be made of any of a variety of materials, including metal, porcelain, ceramics, resin, or a combination thereof. In general, it is desirable for a dental crown to provide the appearance and function of a normal tooth.

When a patient needs a crown, their dentist typically begins by preparing the existing tooth to receive the crown, often by filing the tooth down and/or building it up, if part is missing, to provide a base to support the crown. The dentist then makes an impression of the patient's tooth, either using an impression paste or putty or through digital imaging. The dental crown is made based on the impression. The dentist then evaluates the dental crown by placing it in the patient's mouth atop the prepared existing tooth, subsequently makes any necessary adjustments to the dental crown to improve fit or appearance, and then cements the dental crown in place.

A dental crown is obviously quite small, and thus can be difficult to grasp while making adjustments. This can lead to the dentist dropping the dental crown. Furthermore, if a dentist is holding the dental crown with his or her fingers while adjusting the dental crown with a bur or adjustment wheel, the dentist risks injury if the bur or adjustment wheel slips or gets too close to the dentist's fingers. This can also lead to cross-contamination issues if the bur tears the dentist's glove.

Until 2015, the standard practice was to fabricate dental crowns on a plaster or plastic dental model, which would include a die or handle to hold the crown. This is no longer the case, as current dental crown fabrication is typically completed digitally on a computer and milling unit, and thus does not include a die or handle.

Dentists sometimes use pliers or forceps to separate their fingers from the dental crown and mitigate some of these risks, but such tools often are incapable of holding the dental crown securely enough to prevent movement of the dental crown during adjustments. Furthermore, such tools can be unwieldy and must be disinfected between patents.

Based on the foregoing, it is desirable to provide a dental crown holder that can temporarily hold a dental crown securely while making adjustments to the dental crown.

It is further desirable for the dental crown holder to be disposable to prevent cross-contamination between patients.

It is further desirable for the dental crown holder to be customizable to fit various crown sizes and shapes.

It is further desirable for the dental crown holder to hold the dental crown securely without slipping, rotating, or wobbling.

SUMMARY OF THE INVENTION

In general, in a first aspect, the invention relates to a dental crown holder comprising a handle and a working end, where the working end has at least one extension arm extending therefrom capable of receiving a curable material and capable of fitting within a dental crown. Each of the at least one extension arms may be capable of being bent and/or broken off from the working end.

The dental crown holder may further comprise the curable material. The curable material may be a putty of self-cure or autopolymerizing polysiloxane. The curable material may be capable of initially conforming to an interior (intaglio) surface of the dental crown before setting up to a fixed shape.

In a second aspect, the invention relates to a method of securely holding a dental crown. The method may comprise: selecting a dental crown holder, where the dental crown holder comprises a handle and a working end, where the working end has at least one extension arm extending therefrom; covering the working end of the dental crown holder, including the at least one extension arm, in a curable material; placing the dental crown into the curable material such that at least a portion of the at least one extension arm and at least a portion of the curable material are located inside an interior surface of the dental crown; and curing the curable material.

The method may further comprise, prior to covering the working end of the dental crown holder in curable material, bending or breaking off one or more of the at least one extension arms such that the at least one extension arms are capable of fitting within the interior surface of the dental crown. Additionally or alternately, the method may further comprise removing excess curing material from the dental crown holder and the dental crown.

Additionally or alternately, the method may further comprise holding the handle of the dental crown holder; adjusting the dental crown while holding the handle; and removing the dental crown from the dental crown holder.

Again, the curable material may be a putty of self-cure or autopolymerizing polysiloxane and/or the curable material may be capable of initially conforming to the interior surface of the dental crown before setting up to a fixed shape.

BRIEF DESCRIPTION OF THE DRAWINGS

FIG. 1 is a side view of one embodiment of the dental crown holder;

FIG. 2 is a perspective view of one embodiment of the dental crown holder;

FIGS. 3 through 7 show one embodiment of the dental crown holder in use, with:

FIG. 3 showing a perspective view of the dental crown holder along with a crown and a putty applicator;

FIG. 4 showing a side perspective view of the working end of the dental crown holder ready for use;

FIG. 5 showing a side perspective view of the working end of the dental crown holder with putty thereon;

FIG. 6 showing a side perspective view of the working end of the dental crown holder with putty thereon and a dental crown in place; and FIG. 7 showing a side perspective view of the working end of the dental crown holder with a dental crown in place, with excess putty trimmed away;

FIG. 9b is a side view of the same four alternative embodiments of the dental crown holder, with the view rotated 90 degrees from the view of FIG. 9a.

Figure 8A:
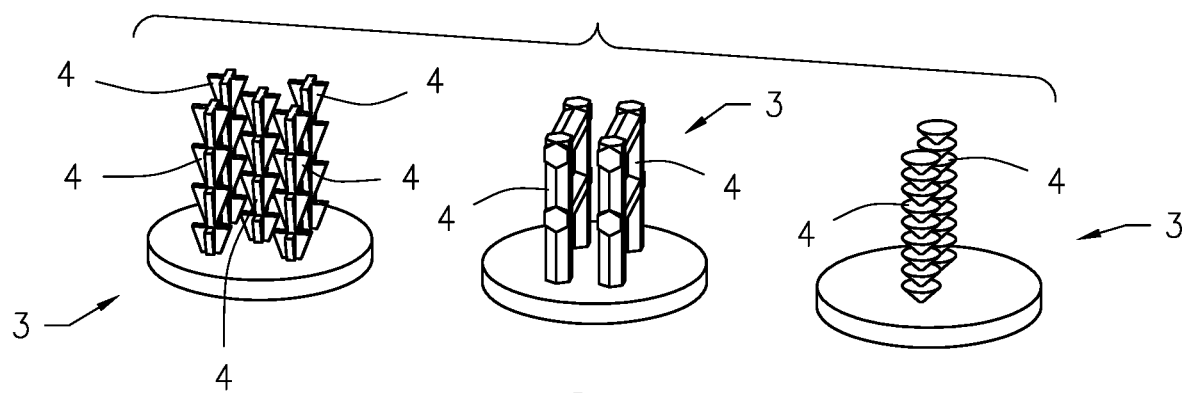
FIG. 8a is a perspective view of three alternative embodiments for the working end of the dental crown holder.

Other advantages and features will be apparent from the following description and from the claims.

DETAILED DESCRIPTION OF THE INVENTION

The devices and methods discussed herein are merely illustrative of specific manners in which to make and use this invention and are not to be interpreted as limiting in scope.

While the devices and methods have been described with a certain degree of particularity, it is to be noted that many modifications may be made in the details of the construction and the arrangement of the devices and components without departing from the spirit and scope of this disclosure. It is understood that the devices and methods are not limited to the embodiments set forth herein for purposes of exemplification.

In general, in a first aspect, the invention relates to a dental crown holder 1. The dental crown holder 1 may be elongate. The dental crown holder 1 may have a handle portion 2 and a working end 3. The handle portion 2 of the dental crown holder 1 may be generally cylindrical, as shown in the drawings, or may have any other desired shape and/or cross section.

Figure 8B:
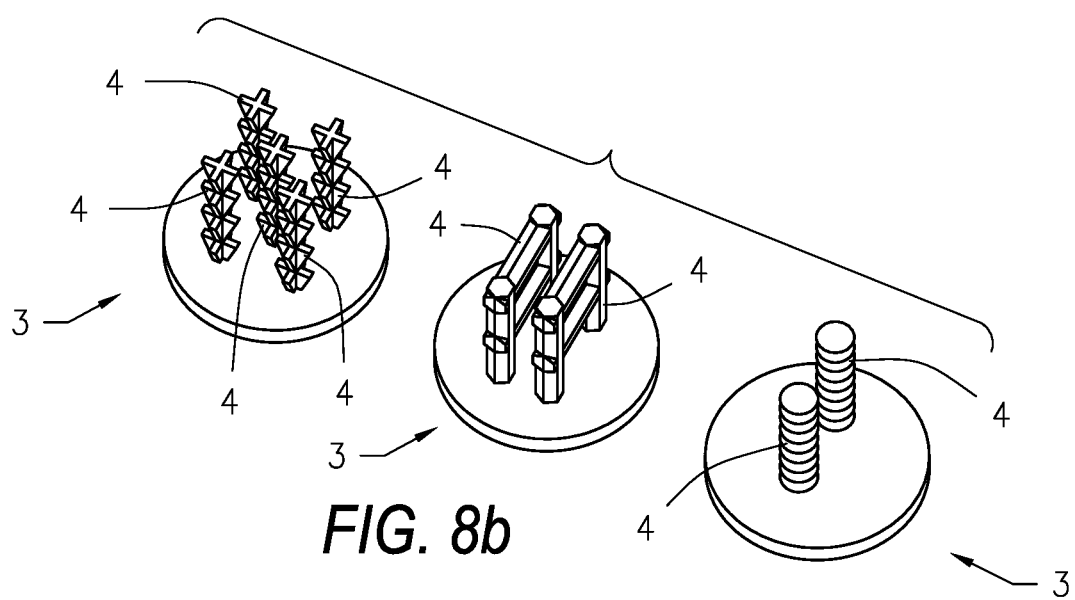
FIG. 8b is a different perspective view of the same three alternative embodiments for the working end of the dental crown holder.
Figure 8C:
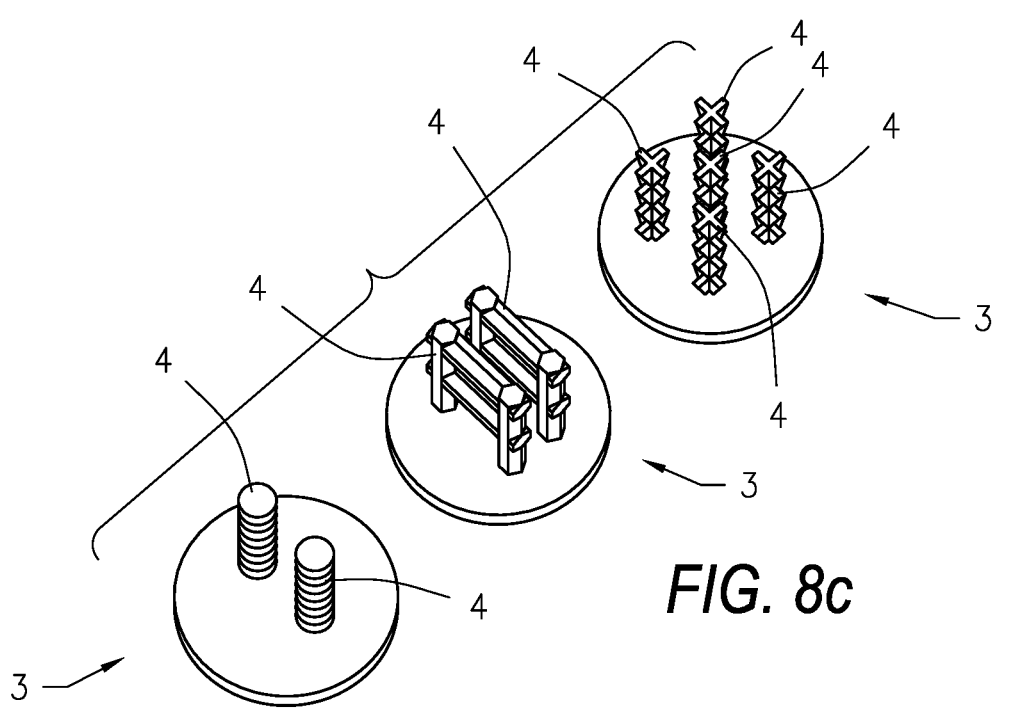
FIG. 8c is a different perspective view of the same three alternative embodiments for the working end of the dental crown holder.
Figure 9A:
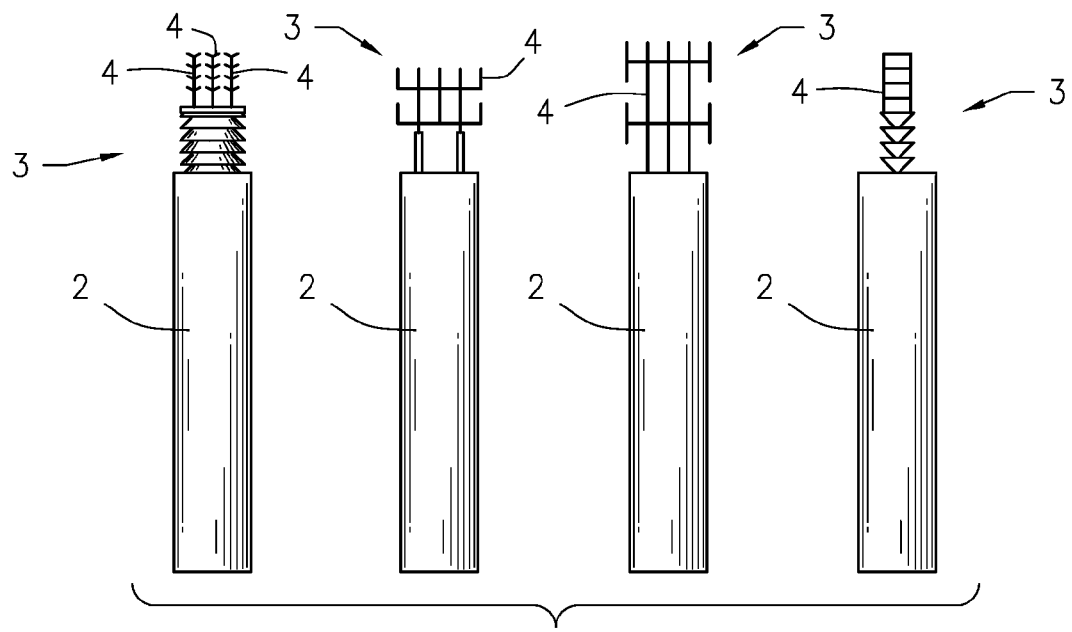
FIG. 9a is a side view of four alternative embodiments of the dental crown holder.
Figure 9B:
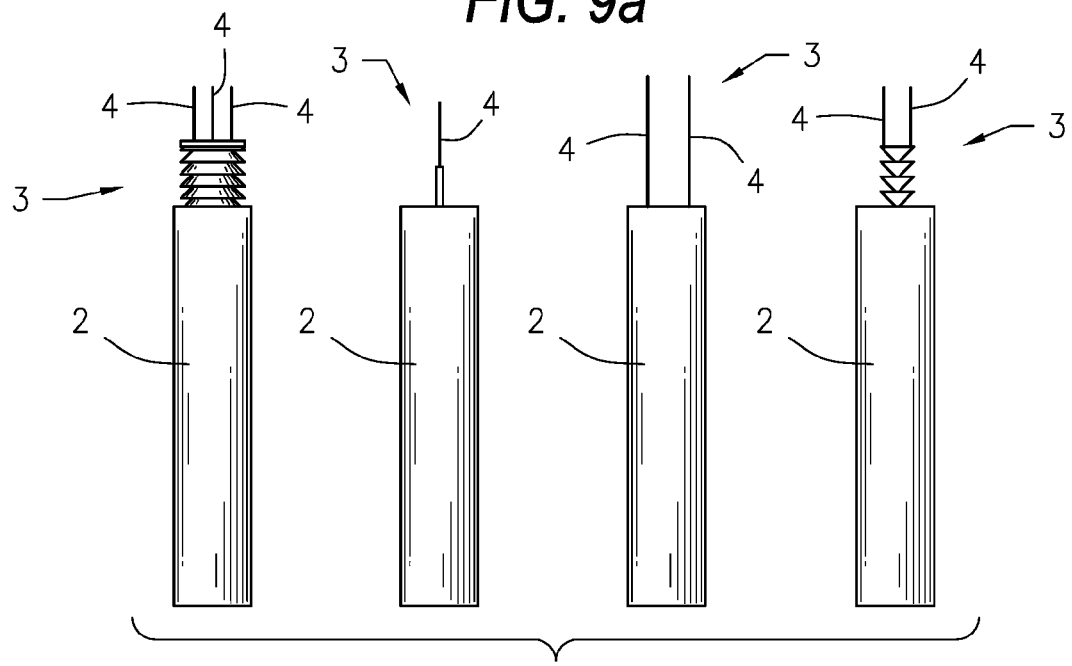
Figure 9C:
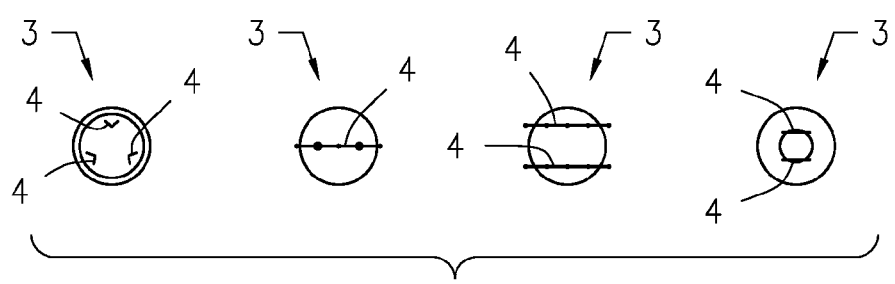
FIG. 9c is a top view of the same four alternative embodiments of the dental crown holder.

The working end 3 of the dental crown holder 1 may have one or more extension arms 4. The extension arms 4 may have any desired shape and configuration. For example, one embodiment of the extension arms 4 is shown in FIGS. 1 through 7; second, third, and fourth embodiments of the extension arms 4 are shown in FIGS. 8a, 8b, and 8c; and fifth, sixth, seventh, and eighth embodiments of the extension arms 4 are shown in FIGS. 9a, 9b, and 9c. The examples provided in the drawings are examples only, and are not limiting of the shapes, sizes, configurations, or quantities of extension arms 4 that may be offered on the dental crown holder 1. The extension arms 4 may be capable of being easily bent or broken off by hand.

The dental crown holder 1, including the handle portion 2 and the working end 3, including the extension arms 4, may be made of any desired material. In particular, the dental crown holder 1 may be made of material that is inexpensive, allowing the dental crown holder 1 to be considered disposable. By way of example, but not limitation, the dental crown holder 1 may be made of plastic, wood, metal, a combination thereof or any other desired material. The entire dental crown holder 1 may be unitarily made, such that the handle portion 2, the working end 3, and the extension arms 4 are one unit and inseparable. If so, all components of the dental crown holder 1 may be made of the same material. Alternately, one or more components may be separately made and/or separable from one or more other components. For example, the working end 3 with the extension arms 4 may be separately made and/or separable from the handle portion 2, and may be permanently or removably attached thereto. If so, all components of the dental crown holder 1 may be made of the same material, one or more components of the dental crown holder 1 may be made of a different material than the other component of the dental crown holder 1, or each component of the dental crown holder 1 may be made of different materials. If the working end 3 with the extension arms 4 is separately made and/or separable from the handle portion 2, the dental crown holder 1 may include a plurality of interchangeable working ends 3. The working ends 3 may, for example, each have a different configuration of extension arms 4 and may each be separately attachable to the handle portion 2, as desired.

During use, a user may begin by selecting a dental crown holder 1 and collecting other items, such as putty 5 and a dental crown 6, as shown in FIG. 3. The dental crown 6 may be a permanent dental crown, or may be a temporary dental crown for the patient to use while a permanent dental crown is being produced. The putty 5 may be any desired shapeable and curable material, such as a putty of self-cure or autopolymerizing polysiloxane or other polymer, light curing resin, or any other desired material. The putty 5 may be capable of initially conforming to the interior (intaglio) surface of the dental crown 6 before setting up to a fixed shape.

If the extension arms 4 of the dental crown holder are capable of being bent or broken off, the user may manipulate the extension arms 4 of the dental crown holder 1 as desired to fit within the interior (intaglio) surface of the dental crown 6, as shown in FIG. 4. While holding the handle 2 of the dental crown holder, the user may place putty 5 on the working end 3 of the dental crown holder 1, completely covering the working end 3 including the extension arms 4, as shown in FIG. 5. The user may then push the dental crown 6 into the putty 5 and onto the working end 3, such that at least a portion of the extension arms 4 and the putty 5 are located inside the interior (intaglio) surface of the dental crown 6, as shown in FIG. 6. The putty 5 may conform to the interior (intaglio) surface of the dental crown 6. Excess putty may be wiped or cut away from the dental crown holder 1 and the dental crown 6, as shown in FIG. 7. The putty 5 may be cured as necessary, depending on the type of putty, such as by allowing the putty 5 to self-cure or by actively curing the putty 5 with a curing light. Once the putty 5 has cured, it may be locked to the dental crown holder 1 by the extending arms and it may have conformed to the exact shape of the interior (intaglio) surface of the dental crown 6.

The dental crown holder 1 with cured putty 5 may thus securely hold the dental crown 6 without any slipping, rotating, or wobbling. This allows the user to make adjustments to the dental crown 6 while holding the handle 2 of the dental crown holder 1 rather than the dental crown 6 itself. This aids in the safety of the user by reducing the chance of personal trauma by keeping the user's fingers further away from the bur or adjustment wheel since the dental crown 6 is not held solely by the user's fingers. It also reduces the chance of a bur tearing a glove of the user and causing a cross-contamination issue between patient saliva and a possible skin abrasion or cut on the use's fingers or hand. The secure hold provided by the dental crown holder 1 also reduces the chance of a dental crown 6 that is being adjusted coming dislodged, flying through the air, and falling to the ground, as often happens when a dental crown 6 is being held solely by the user's fingers or a less secure implement, such as pliers or forceps. All of this leads to greater efficiency of the dental practitioner. Once the dental crown 6 has been sufficiently adjusted, the user may remove the dental crown 6 from the putty 5 on the dental crown holder 1, and the user may dispose of the used dental crown holder 1.

Furthermore, the dental crown holder 1 may be easily held by the user. The dental crown holder 1 may be disposable, thus preventing cross-contamination between patients. The dental crown holder 1 may be customizable, as described above, to fit various crown sizes and shapes.

Whereas, the devices and methods have been described in relation to the drawings and claims, it should be understood that other and further modifications, apart from those shown or suggested herein, may be made within the spirit and scope of this invention.

What is claimed is:

1. A method of securely holding a dental crown comprising:
    selecting a dental crown holder, where the dental crown holder comprises a handle and a working end, where the working end has a plurality of extension arms extending therefrom;
    bending or breaking off one or more of the plurality of extension arms such that the extension arms still extending from the working end are capable of fitting within the interior surface of the dental crown;
    covering the working end of the dental crown holder, including the plurality of extension arms, in a curable material;
    placing the dental crown into the curable material such that at least a portion of the plurality of extension arms and at least a portion of the curable material are located inside an interior surface of the dental crown; and
    curing the curable material.

2. The method of claim 1 further comprising removing excess curing material from the dental crown holder and the dental crown.

3. The method of claim 1 further comprising:
    holding the handle of the dental crown holder;
    adjusting the dental crown while holding the handle; and
    removing the dental crown from the dental crown holder.

4. The method of claim 1 where the curable material is a putty of self-cure or autopolymerizing polysiloxane.

5. The method of claim 1 where the curable material is capable of initially conforming to the interior surface of the dental crown before setting up to a fixed shape.

* * * * *